United States Patent [19]

Wehowsky et al.

[11] Patent Number: 4,766,234

[45] Date of Patent: Aug. 23, 1988

[54] URETHANES WHICH CONTAIN PERFLUOROALKYL GROUPS, EPICHLOROHYDRIN GROUPS AND DIALCOHOL RADICALS, THE PREPARATION AND USE THEREOF

[75] Inventors: Frank Wehowsky, Burgkirchen; Rolf Kleber, Neu-Isenburg; Lothar Jaeckel, Flörsheim am Main, all of Fed. Rep. of Germany

[73] Assignee: Hoechst Aktiengesellschaft, Frankfurt am Main, Fed. Rep. of Germany

[21] Appl. No.: 930,504

[22] Filed: Nov. 12, 1986

[30] Foreign Application Priority Data

Nov. 13, 1985 [DE] Fed. Rep. of Germany ....... 3540147

[51] Int. Cl.$^4$ ........................................... C07C 125/06
[52] U.S. Cl. ..................................... 560/26; 560/115; 560/158; 260/391
[58] Field of Search ..................... 560/26, 115, 158; 260/391

[56] References Cited

U.S. PATENT DOCUMENTS

| 403,657,320 | 4/1972 | Anello | 560/26 |
| 3,681,426 | 8/1972 | Hahn | 560/26 |
| 3,721,700 | 3/1973 | Schuierer | 560/26 |
| 3,746,742 | 7/1973 | Schuierer | 560/26 |
| 3,952,075 | 4/1976 | Nakamura et al. | 260/950 |
| 4,065,630 | 12/1977 | Sandler | 560/26 |
| 4,264,484 | 4/1981 | Patel | 260/29.6 |
| 4,289,892 | 9/1981 | Soch | 560/26 |
| 4,321,404 | 3/1982 | Williams | 560/26 |
| 4,340,749 | 7/1982 | Patel | 560/182 |
| 4,468,527 | 8/1984 | Patel | 564/96 |
| 4,525,305 | 6/1985 | Patel | 560/26 |

FOREIGN PATENT DOCUMENTS 172717 2/1986 European Pat. Off. .
3530967 3/1987 Fed. Rep. of Germany ........ 560/26

Primary Examiner—Michael L. Shippen

[57] ABSTRACT

The novel urethanes, in addition to at least one perfluoroalkyl group, also contain epichlorohydrin groups and dialcohol radicals in the molecule. They are prepared by reacting a fluorine-containing alcohol with epichlorohydrin to give the perfluoroalkyl-epichlorohydrin adduct, reacting this adduct with a di- or triisocyanate to give the perfluoroalkyl-epichlorohydrin-isocyanate adduct and by reacting this adduct with a dialcohol or a monoetherified dialcohol to give the desired urethanes having a perfluoroalkyl group and having epichlorohydrin groups and dialcohol radicals, and by reacting a suitable urethane compound of this type with a perfluoroalkyl-containing di- or triisocyanate to give the desired urethanes having a plurality of perfluoroalkyl groups and having epichlorohydrin groups and. dialcoholradicals. The novel urethanes are preferably used for the oleophobic and hydrophobic finishing of textiles.

3 Claims, No Drawings

URETHANES WHICH CONTAIN PERFLUOROALKYL GROUPS, EPICHLOROHYDRIN GROUPS AND DIALCOHOL RADICALS, THE PREPARATION AND USE THEREOF

The invention relates to urethanes which contain perfluoroalkyl groups, epichlorohydrin groups and dialcohol radicals. The invention further relates to a process for preparing the novel urethane compounds and to their use.

U.S. Pat. Nos. 4,264,484, 4,340,749 and 4,468,527 describe urethanes which contain perfluoroalkyl and epichlorohydrin groups and have the formula below (cf. the formulae I, V and VIII of said patent specifications),

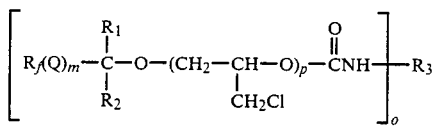

in which
$R_f$ denotes a fluoroaliphatic radical,
Q denotes a divalent group which is free of epoxy-reactive and isocyanate-reactive groups, for example a —CO—, —CONR—, —SO$_2$NR—, —SO$_2$—, p13 $C_nH_{2n}$—, —C$_6$H$_4$—, —C$_6$H$_3$Cl— or —OC$_2$H$_4$— group or combinations thereof, where R is a hydrogen atom or an alkyl radical having 1 to 6 carbon atoms and n is 1 to 20,
m denotes 0 or 1,
$R_1$ denotes a hydrogen atom or a lower alkyl radical,
$R_2$ denotes a hydrogen atom, a lower alkyl radical or an aryl radical having 6 to 12 carbon atoms, or $R_1$ and $R_2$ are bonded to each other to form an aromatic or cycloaliphatic structure,
p denotes a number having a small value, for example 1 to 5,
o denotes a number which is equal to the number of isocyanate groups in the isocyanate, for example 2 to 5, and
$R_3$ denotes the isocyanate-free radical of an organic polyisocyanate, such as 2,4-toluylene diisocyanate.

These urethanes are recommended for use as oil- and water-repellent agents for textiles.

U.S. Pat. Nos. 3,721,700 and 3,952,075 describe urethanes which contain perfluoroalkyl groups and dialcohol radicals.

The urethanes disclosed in U.S. Pat. No. 3,721,700 conform to the general formula

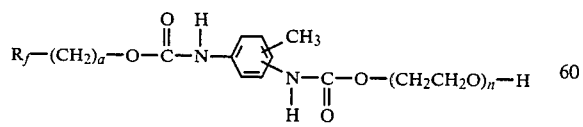

in which $R_f$ is a perfluorinated alkyl radical having 3 to 12 carbon atoms, n is a number from 4 to 70 and a is 1 or 2.

The urethanes disclosed in U.S. Pat. No. 3,952,075 conform to the general formula

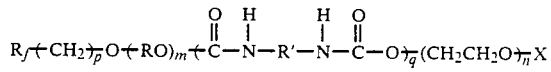

in which $R_f$ is a perfluoroalkyl group having 4 to 14 carbon atoms, R is an alkylene group having 2 to 4 carbon atoms, R' is an alkylene or arylene group having 2 to 8 carbon atoms, X is the hydrogen atom, PO$_3$H$_2$ or SO$_3$H, p is 1 to 10, m and n are 0 or 1 to 50 and q is 0 or 1.

The indicated urethanes are described in the two U.S. patents as oil- and water-repellent agents for textiles and as dispersants for preparing aqueous dispersions of polymeric, fluorine-containing ethyleneimine derivatives.

It has now been found, surprisingly, that perfluoroalkylated urethanes have particularly excellent properties with respect to the finishing of textiles in oil-, water- and dirt-repellency when, in addition to at least one perfluoroalkyl group, they also contain epichlorohydrin groups and a dialcohol component in the molecule. The urethane compounds according to the invention conform to the following general formula 1

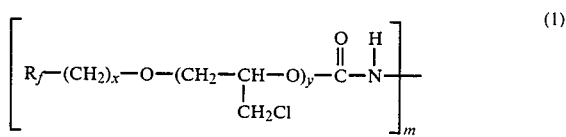

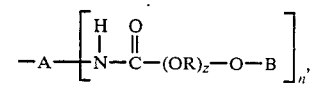

in which
$R_f$ denotes a perfluoroalkyl group having 4 to 20 carbon atoms, preferably 6 to 16 carbon atoms, or an $R'_fSO_2NR_1$ group in which $R'_f$ has one of the meanings of $R_f$ and $R_1$ is H or an alkyl group having 1 to 4 carbon atoms,
x is a whole number from 1 to 4, preferably 2,
y is a number from 1 to 10, preferably 1 to 5,
z is a number from 1 to 25, preferably 1 to 20,
m is a number from 1 to 2 and
n is a number from 1 to 2, the total of m+n being at most 3,
A denotes one of the groups conforming to the following formulae 2 to 10 (which are isocyanate-free radicals):

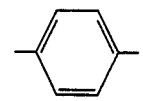
(2)

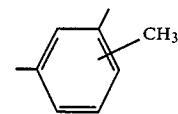
(3)

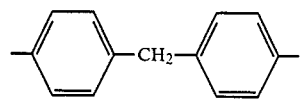
(4)

-continued

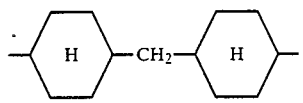  (5)

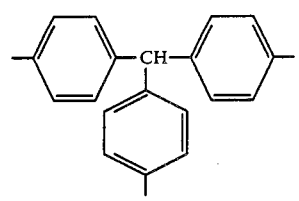  (6)

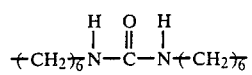  (7)

  (8)

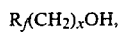  (9)

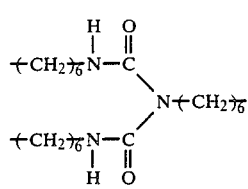  (10)

R denotes an alkylene group having 2 to 6 carbon atoms, preferably 2 to 4 carbon atoms, the chloromethylethylene group or a group of the formula —CH(CH$_2$OCH$_2$CH$_2$R$_F$)—CH$_2$— (R$_F$=C$_4$F$_9$ to C$_{20}$F$_{41}$, preferably C$_6$F$_{13}$ to C$_{16}$F$_{33}$), where R can also have more than one of these meanings when z is greater than 1, and B denotes the hydrogen atom, an alkyl group having 1 to 4 carbon atoms or a group conforming to the following formula 11

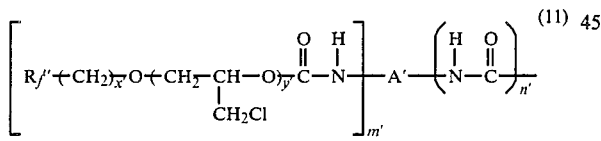  (11)

in which R$_f''$, x', y', m', n' and A' have one of the meanings of R$_f$, x, y, m, n and A.

R$_f$ is preferably the perfluoroalkyl group mentioned. This group can be straight-chain or branched, preferably terminally branched. The straight-chain perfluoroalkyl radicals are preferred. The perfluoroalkyl radical is in general a mixture of perfluoroalkyl groups having the abovementioned number of carbon atoms.

A is preferably a toluylene group or one of the three groups conforming to the formulae 8 to 10 (these three groups are generally present as a mixture).

R is preferably the ethylene, propylene, butylene or the chloromethylethylene group: —CH(CH$_2$Cl)—CH$_2$—, where R can also have more than one of these meanings if z>1; in that case, R is preferably the ethylene and propylene group.

B is preferably hydrogen, a group which conforms to the formula 11, where A' is a toluylene group or one of the three groups conforming to the formulae 8 to 10, or an alkyl group having 1 to 4 carbon atoms.

The preparation of the urethanes according to the invention, which contain perfluoroalkyl groups, epichlorohydrin groups and dialcohol radicals, follows from the general formula 1. The novel urethanes are preferably prepared by reacting a fluorine-containing alcohol of the formula R$_f$(CH$_2$)$_x$OH, in which R$_f$ and x have the abovementioned meaning, with epichlorohydrin to give the perfluorohydroalkanolepichlorohydrin adduct or perfluorosulfonamidoalkanolepichlorohydrin adduct of the formula

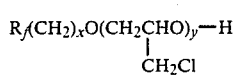  (Adduct 1)

in which R$_f$, x and y have the abovementioned meaning, by reacting adduct 1 with a di- or triisocyanate conforming to one of the groups of the formulae 2 to 10 to give the perfluoroalkyl-epichlorohydrin-isocyanate adduct of the formula

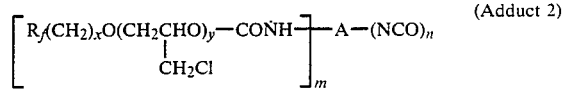  (Adduct 2)

in which R$_f$, x, y, m and n have the abovementioned meaning, and by reacting adduct 2 with a dialcohol (diol) or a monoetherified diol of the following formulae

in which R and z have the abovementioned meaning and B is the hydrogen atom or an alkyl group having 1 to 4 carbon atoms, to give the desired urethanes which contain perfluoroalkyl and epichlorohydrin groups and dialcohol radicals and have the two following formulae 12 and 13

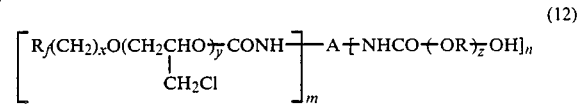  (12)

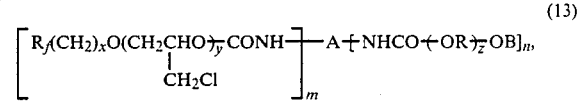  (13)

in which R$_f$, x, y, z, m, n, A and B have the abovementioned meaning, and by reacting a urethane of the formula 12 with an isocyanate compound which contains one or more free isocyanate groups and conforms to the group of the formula 11 to give the desired urethanes which contain perfluoroalkyl and epichlorohydrin groups and contain dialcohol radicals and have the following formula 14

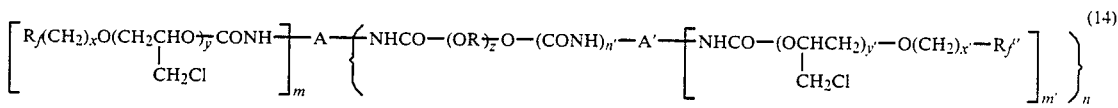

in which $R_f$, $R_f'$, $x'$, $y$, $y'$, $z$, $m$, $m'$, $n$, $n'$, A, A' and R have the abovementioned meaning.

In what follows, the preparation of the compounds according to the invention is described in detail.

To prepare adduct 1, i.e. the perfluorohydroalkanolepichlorohydrin adduct or the perfluorosulfonamidoalkanolepichlorohydrin adduct, the preferred procedure is to react the fluorine-containing alcohol, for example perfluoroalkylethanol or perfluoroalkylsulfonamidoethanol, with epichlorohydrin (boiling point under normal conditions 116° C.), if desired in the presence of Lewis acids as catalyst, at a temperature of 30° to 100° C., preferably 40° to 70° C., the fluorine-containing alcohol and the epichlorohydrin being used in a molar ratio of about 1:y (y has the abovementioned meaning). The perfluorohydroalkanol and perfluorosulfonamidoalkanol are in general, in relation to the perfluoroalkyl radical, inexpensive, commercially available mixtures having essentially 6 to 16 carbon atoms. The nature of the Lewis acid is not critical. Preference is given to $BF_3$, boron trifluoride diethyl etherate, $SnCl_4$, $SbCl_5$, $TiCl_4$, $FeCl_3$, $PF_5$ and/or dibutyltin dilaurate, boron trifluoride diethyl etherate being particularly preferred. The amount of catalyst is in general 0.01 to 5% by weight, preferably 0.1 to 1% by weight, based on perfluoroalkylethanol. The reaction is preferably carried out with stirring and under autogenous pressure. The reaction takes from about 0.5 to 7 hours. It can be expedient to use a solvent. Preferred solvents are halogenated hydrocarbons such as carbon tetrachloride, trichloroethylene, 1,2-dichloroethane, trichloroethane, pentafluoromonochloroethane and trifluorodichloroethane; ketones such as methyl ethyl ketone and cyclohexanone; ethers such as diisopropyl ether and tetrahydrofuran; dimethylformamide and N-methylpyrrolidone. The reaction in question proceeds quantitatively. In the reaction product obtained, the solvent, if used, is distilled off, together with any volatiles present, such as unconverted epichlorohydrin. For reasons of expediency the distillation can also be carried out under reduced pressure (water jet vacuum). The Lewis acid used as catalyst, although it would not interfere in the subsequent reaction with toluylene diisocyanate, can be washed away or neutralized by means of alkaline agents, preferably by means of an aqueous sodium bicarbonate solution or an amine such as triethylamine. Adduct 1 is a waxy, yellow product.

Adduct 2 is preferably prepared by reacting adduct 1 with an isocyanate conforming to the formulae 2 to 10 at a temperature of 70° to 150° C., preferably 90° to 130° C., the adduct 1 compound and the isocyanate being used in the molar ratio which follows from the desired meaning for m and n in the formula for adduct 2. The reaction is preferably carried out with stirring and under autogenous pressure and, if expedient, for example to shorten the reaction time, in the presence of the abovementioned Lewis acid catalysts. It is also possible to use the abovementioned solvents. The reaction takes from 1 to 15 hours. The isocyanate will frequently comprise commercially available isocyanate mixtures. For instance, the toluylene diisocyanate is in general about 80% by weight 2,4-toluylene diisocyanate and 20% by weight 2,6-toluylene diisocyanate. The isocyanates conforming to the groups of the formulae 8 to 10 are likewise generally present as mixtures. A commercially available and preferred mixture of this type comprises three isocyanates in question, the isocyanate conforming to the formula 10 being present in an amount of at least 50% by weight, based on the mixture (in this mixture the isocyanate conforming to the formula 10 is thus the main component). The reaction of adduct 1 with isocyanate to give the abovementioned adduct 2 proceeds quantitatively. The products obtained can be purified, if necessary, for example by distilling off volatiles. Adduct 2 is a waxy, yellow product.

The compounds according to the invention of the formulae 12 and 13 are preferably prepared by reacting adduct 2 with a diol or a monoetherified diol of the abovementioned kind at a temperature of 70° to 150° C., preferably 90° to 130° C., the adduct 2 compound and the diol or the diol monoether being used in such a molar ratio that the molar amount of diol or diol ether corresponds to the free isocyanate groups present in the adduct 2 used. The reaction is preferably carried out with stirring and under autogenous pressure and, if expedient, for example to shorten the reaction time, in the presence of the abovementioned Lewis acid catalysts. It is also possible to use the abovementioned solvents. The reaction takes from 1 to 15 hours. The reaction of adduct 2 with the diol or the diol monoether to give the compounds according to the inventin of the formulae 12 and 13 proceeds quantitatively. The product obtained can be purified, if necessary, for example by distilling off volatiles. The compounds according to the invention of the formulae 12 and 13 are waxy, yellow to brown products.

The compounds according to the invention of the formula 14 are preferably prepared by reacting a compound of the formula 12 with an isocyanate compound conforming to the group of formula 11 (compare adduct 2) at a temperature of 70° to 150° C., preferably 90° to 130° C., the compound of the formula 12 and the isocyanate compound being used in such a molar ratio that the molar amount of isocyanate compound corresponds to the free OH groups present in the compound of the formula 12. As for the rest, the preparation of these compounds according to the invention is likewise subject to the above statements about the preparation of the compounds according to the invention of the formulae 12 and 13. The compounds according to the invention of the formula 14 are like those of the formulae 12 and 13 waxy, yellow to brown products.

The compounds according to the invention are surprisingly good textile treatment agents. They impart to the textiles in particular excellent hydrophobic and oleophobic properties. They further have to a high extent the property of resisting without any loss of activity the high stresses to which the finished textiles are exposed, for example in the course of drawing, texturing, and in particular in the course of dyeing and washing. An unexpected and particularly great advantage of the compounds according to the invention is that they can even be used in conventional textile treatment finishes, for example in spin finishes, without losing their excellent activity.

The textile material can be of natural and/or synthetic origin. It preferably comprises polyamide, polyester and/or polacrylonitrile, of which polyamide is particularly preferred. The textile material can be present in any desired form, for example as filament, fiber, yarn, woven fabric, knitted fabric, carpet or bonded fiber web. The add-on level of compounds according to the invention is so chosen that 0.02 to 1% by weight of fluorine, preferably 0.04 to 0.4% by weight of fluorine, are present on the textile material, calculated from the amount of fluorine in the compounds according to the invention; weight percentages are based on the treated textile material. The treatment of the textile material with the urethanes according to the invention is in general effected either via the abovementioned textile treatment finishes, into which the urethanes according to the invention have been incorporated, or by means of solutions, emulsions or dispersions which have been specially prepared from the urethanes. In the solutions, emulsions or dispersions on the one hand and in the textile treatment finishes on the other they are generally present in a concentration of 5 to 40% or 0.5 to 5% by weight respectively, preferably 8 to 30% or 1 to 3% by weight respectively. The treatment of the textiles with the solutions, emulsions or dispersions mentioned is carried out by customary methods, for example by spraying, dipping, padmangling and the like. Subsequently the impregnated textile material is dried and subjected to a heat treatment. The heat treatment is generally carried out by heating the textile material to a temperature of 130° to 200° C. and maintaining it at that temperature for 10 seconds to 10 minutes. The textile material finished with the urethanes according to the invention has the abovementioned excellent properties.

The invention will now be explained in more detail by reference to examples.

Compounds according to the invention

EXAMPLE 1

A glass flask equipped with a stirrer, reflux condenser, thermometer, dropping funnel and hot bath was charged with 527.9 g (1.0 mol) of a commercially available perfluoroalkylethanol mixture with perfluoroalkyl=$C_6F_{13}$ to $C_{12}F_{25}$ (OH number=106), 380 ml of 1,2,2-trifluorotrichloroethane ($CFCl_2$—$CF_2Cl$; boiling point=48° C.) as solvent and 5.0 g of boron trifluoride diethyl etherate as catalyst (i.e. 1% by weight of catalyst, based on perfluoroalkylethanol). To this solution were added dropwise at 45° C. 166.5 g (1.8 mol) of epichlorohydrin, and the mixture was then maintained at the boiling point of the solvent for 3 hours. The solvent used was then distilled off in vacuo (water jet vacuum). A waxy yellow product is present (adduct 1). This adduct is a perfluoroalkylethanol-epichlorohydrin adduct having the molar ratio of perfluoroalkylethanol-:epichlorohydrin equal to 1:1.8 (i.e. y in the formula 1 is 1.8). The same method was also used to prepare the adducts 1 used in the examples below.

In what follows, the approach for the further reactions for preparing the compounds according to the invention is summarized. These reactions were in each case carried out in a glass flask equipped with a stirrer, reflux condenser with drying tube, thermometer and hot bath.

Starting mixture:

100.0 g (0.144 mol) of adduct 1
25.1 g (0.144 mol) of toluylene diisocyanate, more specifically a mixture of about 80% by weight of 2,4- and about 20% by weight of 2,6-toluylene diisocyanate (i.e. a commercial product) 82.5 g (0.144 mol) of hexaepichlorohydrin:

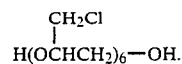

Adduct 1 compound, toluylene diisocyanate and hexaep:chlorohydrin were thus used in a molar ratio of 1:1:1.

Method

The adduct 1 compound and the toluylene diisocyanate were introduced first. The mixture was heated to 100 110° C., maintained at that temperature for 3 hours with stirring and then cooled down (1st reaction step). The perfluoroalkylethanol-epichlorohydrin-toluylene diisocyanate adduct obtained was a waxy, yellow product. To this product in the glass flask was added the hexaepichlorohydrin. The mixture was heated to 100°–110° C., maintained at that temperature for 3 hours with stirring and then cooled down (2nd reaction stage) A waxy, brown product was obtained (yield 206.1 g, i.e. 99.3% by weight of theory). The overall composition of the compound according to the invention obtained conforms to the formula of serial number B1 given in the table following the examples.

EXAMPLE 2

Starting mixture:
69 4 g (0.1 mol) of adduct 1 as per Example 1
17.4 g (0.1 mol) of toluylene diisocyanate as per Example 1
20.3 g (0.1 mol) of diepichorohydrin.

Adduct 1 compound, toluylene diisocyanate and diepichlorohydrin were thus used in a molar ratio of 1:1:1.

Method

The method followed was analogous to that of Example 1. A waxy, brown product was obtained (yield: 105.2 g, i.e. 98.1% by weight of theory). The overall composition of the compound according to the invention obtained conforms to the formula of serial number B2 in the table mentioned.

EXAMPLE 3

Starting mixture:
133.2 g (0.2 mol) of adduct 1 as per Example 1
54.4 g (0.2 mol) of diphenylmethane 4,4'-diisocyanate (a commercial product)
114.6 g (0.2 mol) of hexaepichlorohydrin.

Adduct 1 compound, diphenylmethane diisocyanate and hexaepichlorohydrin were thus used in a molar ratio of 1:1:1.

Method

The diisocyanate was introduced first and melted by heating, and to the diisocyanate melt was added with stirring the molten adduct 1 compound. The mixture was heated to 110°–120° C., maintained at that temperature for 3 hours with stirring and then cooled down (1st reaction stage). The perfluoroalkylethanol-epichlorohydrin-diphenylmethane diisocyanate adduct obtained was a waxy, yellow product. To this product in the glass flask was added the hexaepichlorohydrin. The mixture was heated to 110°–120° C., maintained at that temperature for 4 hours with stirring and subsequently cooled down (2nd reaction stage). A waxy, brown product was obtained (yield 298.6 g, i.e. 98.8% of theory). The overall composition of the compound according to the invention obtained conforms to the formula of serial number B3 in the table mentioned.

EXAMPLE 4

Starting mixture:
310.0 g (0.442 mol) of adduct 1 as per Example 1
377.0 g (0.221 mol) of triphenylmethane 4,4′,4″-triisocyanate
24.4 g (0.221 mol) of 1-chloromethyl-1,2-dihydroxyethane:

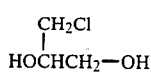

Adduct 1 compound, triisocyanate and the diol compound were thus used in a molar ratio of 2:1:1.

Method

The method followed was analogous to that of Example 3, except that in the first reaction stage the mixture was maintained as 110°–120° C. for 5 hours, in place of the hexaepichlorohydrin the abovementioned chloropropanediol was added and in the second reaction stage the mixture was maintained at 120°–130° C. for 8 hours. A waxy, brown product was obtained (yield 709 g, i.e. 99.7% by weight of theory). The overall composition of the compound according to the invention obtained conforms to the formula of serial number B4 in the table mentioned.

EXAMPLE 5

Starting mixture:
150.0 g (0.225 mol) of adduct 1 as per Example 1
115.3 g (0.150 mol) of triisocyanate conforming to the formula 10, more specifically a mixture of the three isocyanates conforming to the formulae 8, 9 and 10, with the triisocyanate as the main constituent (this is a commercial product)
129.0 g (0.225 mol) of hexaepichlorohydrin.

Adduct 1 compound, isocyanate and hexaepichlorohydrin were thus used in a molar ratio of 3:2:3.

Method

The isocyanate and 1.2 g of dibutyltin dilaurate as catalyst (i.e. 1% by weight, based on the amount of isocyanate used) were introduced first and melted by heating, and to the molten mixture was added with stirring the molten adduct 1 compound. The mixture was maintained at 65° C. for 4 hours with stirring and then cooled down (1st reaction stage). The perfluoroalkylethanol-epichlorohydrin-isocyanate adduct obtained was a waxy, yellow product. To this product in the glass flask was added the hexaepichlorohydrin. The mixture was heated to 100°–110° C., maintained at that temperature for 4 hours with stirring and then cooled down (2nd reaction stage). A waxy, brown product was obtained (yield 371.5 g, i.e. 94.2% by weight of theory). The overall composition of the compound according to the invention obtained conforms to the formula B5.

EXAMPLE 6

Starting mixture:
105.6 g (0.13 mol) of perfluoroalkylethanol-epichlorohydrin adduct having the molar ratio perfluoroalkylethanol:epichlorohydrin equal to 1:3 (i.e. y in the formula 1 is 3) as adduct 1. The perfluoroalkylethanol was a commercially available mixture with perfluoroalkyl=$C_8F_{17}$ to $C_{16}F_{33}$ (OH number=69).
34.4 g (0.13 mol) of dicyclohexylmethane 4,4′-diisocyanate (which is a commercial product)
82.3 g (0.13 mol) of polytetrahydrofuran of molecular weight 650: $H(OC_4H_8)_{8.5}$—OH.

Adduct 1 compound, dicyclohexylmethane diisocyanate and the polytetrahydrofuran (diol) were thus used in the molar ratio 1:1:1.

Method

The method followed was analogous to that of Example 3, except that instead of the hexaepichlorohydrin the above-mentioned polytetrahydrofuran was added, affording a waxy, brown product (yield: 220.5 g, i.e. 99.2% by weight of theory). The overall composition of the compound according to the invention obtained conformed to the formula B6.

EXAMPLE 7

Starting mixture:
81.3 g (0.10 mol) of adduct 1 as per Example 6
28.5 g (0.05 mol) of triisocyanate as per Example 5
31.7 g (0.05 mol) of polytetrahydrofuran as per Example 6.

Adduct 1, triisocyanate and polytetrahydrofuran were thus used in a molar ratio of 2:1:1.

Method

The method followed was analogous to that of Example 1, except that in place of the hexaepichlorohydrin the abovementioned polytetrahydrofuran was added and in the second reaction stage the mixture was maintained at 100°0 to 110° C. for 7 hours, affording a waxy, brown product (yield: 138.4 g, i.e. 98.2% by weight of theory). The overall composition of the compound according to the invention obtained conforms to the formula B7.

EXAMPLE 8

Starting mixture:
97.5 g (0 12 mol) of adduct 1 as per Example 6
34.2 g (0.06 mol) of triisocyanate as per Example 5
58.0 g (0.06 mol) of monoetherified diol of the formula

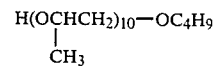

Adduct 1, triisocyanate and decapropylene glycol mono-nbutyl ether were thus used in a molar ratio of 2:1:1.

Method

The method followed was analogous to that of Example 1, except that in the first reaction stage the mixture was maintained at 100° to 110° C. for 6 hours, instead of the hexaepichlorohydrin the abovementioned diol monoether was added and in the second reaction stage the mixture was maintained at 100° to 110° C. for 8 hours, affording a waxy, brown product (yield 184 g, i.e. 97.2% by weight of theory). The overall composition of the compound according to the invention obtained conforms to the formula B8.

49.3 g (0.05 mol) of compound of the following formula $$(C_8F_{17}-C_{16}F_{33})-CH_2CH_2O-(CH_2CHO)_3-CONH-\underset{CH_3}{\underset{|}{\bigcirc}}-N=C=O$$
$$\underset{CH_2Cl}{|}$$

The molar ratio of the compounds used was thus 2:1:1:1.

Method

The method followed was analogous to that of Example 10, the monoethylene glycol being added in the 2nd reaction stage. To the waxy, brown product obtained (which corresponds to the compound according to the invention prepared in Example 7) were added 0.05 mol of the above-indicated perfluoroalkylethanol-epichlorohydrin-isocyanate adduct, which had been obtained by reacting 0.1 mol of adduct 1 compound with 0.05 mol of toluylene diisocyanate. The mixture was maintained at 100° to 110° C. for 3 hours with stirring and then cooled down (3rd reaction stage). A waxy, brown product was obtained (yield 160.7 g, i.e. 99.1% by weight of theory). The overall composition of the compound according to the invention obtained conforms to the formula B11.

EXAMPLE 9

Starting mixture:
81.3 g (0.10 mol) of adduct 1 as per Example 6
28.5 g (0.05 mol) of triisocyanate as per Example 5
54.7 g (0.05 mol) of monoetherified diol of the formula $$H(OCHCH_2)_{10}-(OCH_2CH_2)_{10}-OC_4H_9$$
$$\underset{CH_3}{|}$$

Adduct 1, triisocyanate and deca(propylene-ethylene) glycol mono-n-butyl ether were thus used in a molar ratio of 2:1:1.

Method

The method followed was analogous to that of Example 5, except that in the first reaction stage the mixture was maintained at 100° to 110° C. for 6 hours, instead of hexaepichlorohydrin the abovementioned diol monoether was added and in the second reaction stage the mixture was maintained at 100° to 110° C. for 10 hours, affording a waxy, brown product (yield 161.7 g, i.e. 98.3% by weight of theory). The overall composition of the compounds according to the invention obtained conforms to the formula B9.

EXAMPLE 10

Starting mixture:
162.6 g (0.20 mol) of adduct 1 as per Example 6
57.0 g (0.10 mol) of triisocyanate as per Example 5
64.1 g (0.05 mol) of polytetrahydrofuran as per Example 6.

The molar ratio of the compounds used was thus 4:2:1.

Method

The adduct 1 compound and the triisocyanate were introduced first. The mixture was heated to 100°–110° C. and maintained at that temperature for 3 hours with stirring (1st reaction stage). To the waxy, yellow perfluoroalkylethanol-epichlorohydrin-isocyanate adduct obtained was added the polytetrahydrofuran. The mixture was maintained at 100° to 110° C. for 4 hours with stirring and then cooled down (2nd reaction stage). A waxy, brown product was obtained (yield 278.2 g, i.e. 98.1% by weight of theory). The overall composition of the compound according to the invention obtained conforms to the formula B10.

EXAMPLE 11

Starting mixture:
81.3 g (0.10 mol) of adduct 1 as per Example 6
28.5 g (0.05 mol) of triisocyanate as per Example 5
3.1 g (0.05 mol) of monoethylene glycol

EXAMPLE 12

Starting mixture:
1.3 g (0.10 mol) of adduct 1 as per Example 6
28.5 g (0.05 mol) of triisocyanate as per Example 5
5.8 g (0.05 mol) of 1,6-hexanediol.

The molar ratio of the compounds used was thus 2:1:1.

Method

The method followed was analogous to that of Example 7, except that instead of the polytetrahydrofuran the above-mentioned 1,6-hexanediol was used, affording a waxy, brown product (yield 114.3 g, i.e. 98.8% by weight of theory). The overall composition of the compound according to the invention obtained conforms to the formula B12.

EXAMPLE 13

Starting mixture:
162.6 g(0.20 mol) of adduct 1 as per Example 6
57.0 g (0.10 mol) of triisocyanate as per Example 5
9.0 g (0.10 mol) of 1,4-butanediol.

The molar ratio of the compounds used was thus 2:1:1.

Method

The method followed was analogous to that of Example 12, affording a waxy, ocher product (yield 226.5 g, i.e. 99.1% by weight of theory). The overall composition of the compound according to the invention obtained conforms to the formula B13.

EXAMPLE 14

Starting mixture:
162.6 g (0.20 mol) of adduct 1 as per Example 6
57.0 g (0.10 mol) of triisocyanate as per Example 5
27.1 g (0.05 mol) of fluorinated etherdiol compound of the formula:

HOCH—CH$_2$OH
|
CH$_2$OCH$_2$CH$_2$C$_8$F$_{17}$.

The molar ratio of the compounds used was thus 4:2:1.

Method

The adduct 1 compound and the triisocyanate were introduced first. The mixture was heated to 110° C. and maintained at that temperature for 4 hours with stirring, 4 drops of dibutyltin dilaurate were then added, and the mixture was maintained at 110° C. for a further 3 hours with stirring (1st reaction stage, compare Example 10). To the waxy, yellow perfluoroalkylethanol-epichlorohydrin-isocyanate adduct obtained was added the fluorinated etherdiol compound dissolved in 55 g of di-n-butyl adipate. The mixture was maintained at 110° C. for 5 hours with stirring and then cooled down (2nd reaction stage). A waxy, brown product was obtained (yield 300 g, i.e. 99.5% by weight of theory). The overall composition of the compound according to the invention obtained conformed to the formula B 14.

TABLE

| No. | Chemical formulae of the compounds according to the invention of Examples 1 to 14 |
|---|---|
| B1 | 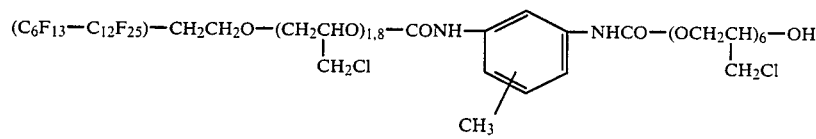 |
| B2 | 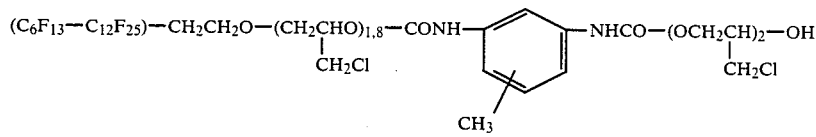 |
| B3 | 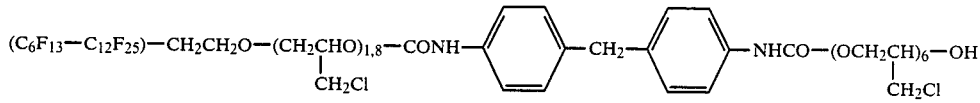 |
| B4 | 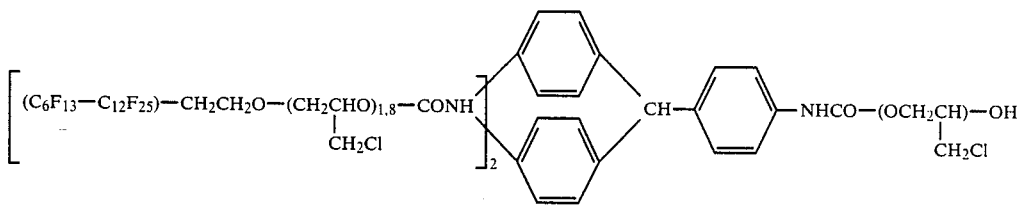 |
| B5 | 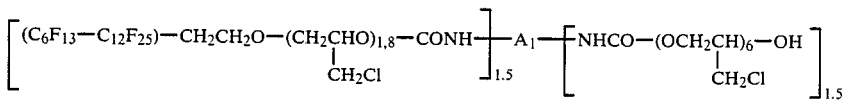 |
| B6 | 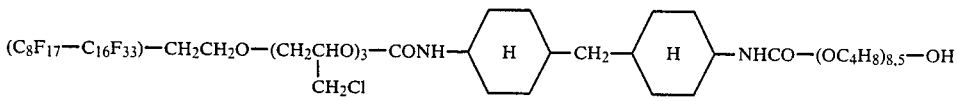 |
| B7 | 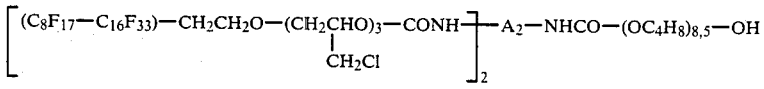 |
| B8 | 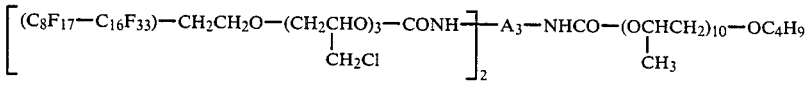 |
| B9 |  |
| B10 | 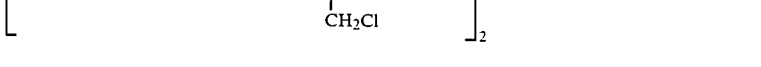 |

TABLE-continued

| No. | Chemical formulae of the compounds according to the invention of Examples 1 to 14 |
|---|---|

B11
$$\left[(C_8F_{17}-C_{16}F_{33})-CH_2CH_2O-(CH_2CHO)_3-CONH-\right]_2 A_6-NHCO-(OC_2H_4)-OB_2$$
$$\hspace{3cm} | \hspace{3cm}$$
$$\hspace{3cm} CH_2Cl$$

B12
$$\left[(C_8F_{17}-C_{16}F_{33})-CH_2CH_2O-(CH_2CHO)_3-CONH-\right]_2 A_7-NHCO-(OC_6H_{12})-OH$$
$$\hspace{3cm} | \hspace{3cm}$$
$$\hspace{3cm} CH_2Cl$$

B13
$$\left[(C_8F_{17}-C_{16}F_{33})-CH_2CH_2O-(CH_2CHO)_3-CONH-\right]_2 A_8-NHCO-(OC_4H_8)-OH$$
$$\hspace{3cm} | \hspace{3cm}$$
$$\hspace{3cm} CH_2Cl$$

B14
$$\left[(C_8F_{17}-C_{16}F_{33})-CH_2CH_2O-(CH_2CHO)_3-CONH-\right]_2 A_9-NHCO-(OCHCH_2)-OB_3$$
$$\hspace{3cm} | \hspace{4cm} |$$
$$\hspace{3cm} CH_2Cl \hspace{3cm} CH_2OC_2H_4C_8F_{17}$$

In the formulae B5 and B7 to B14, $A_1$ to $A_9$ stands for

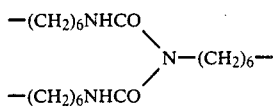

(cf. above mentioned formula 10).

In the formulae B10, B14 and B11
$B_1$ stands for

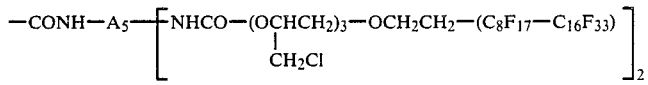

$B_3$ for

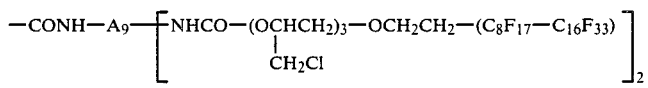

and
$B_2$ for

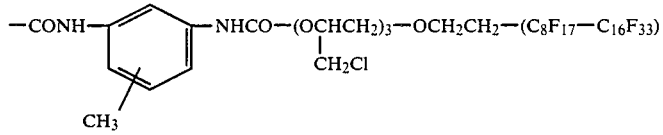

Use of the compounds according to the invention

EXAMPLES I TO XIV

These examples were used to test the compounds according to the invention B1 to B14.

In Examples I to VI, compounds B1 to B6 were tested by means of a specially prepared solution which in each case comprised about 1.2 g of compound according to the invention and 250 g of acetone (acetonic solution of the liquor). Each of the six acetonic liquors was used to treat an identical nylon-6 filament fabric in each case in order to apply to the fabric sufficient of the compound according to the invention that 0.05% by weight of fluorine was present on the fabric (fluorine add-on), percentages by weight being based on the weight of the fabric. To this end the fabric was dipped in conventional manner into the liquor and brought with a pad-mangle to a wet pickup of 30 to 40% by weight, and the acetone-moist fabric was initially air-dried and then held at a temperature of 200° C. for 30 seconds (heat treatment, also referred to as condensation). After this treatment six fabrics with the compounds according to the invention B1 to B6 were present, on each fabric a fluorine add-on of 0.05% by weight being present, per cent by weight being based on the weight of the fabric.

The six fabrics were subjected to the oil repellency (oleophobic properties) test in accordance with AATCC test standard 118—1966 and to the water repellency (hydrophobic properties) test in accordance with DIN 53,888—1965, after the condensation described and after a three-hour treatment of the condensed fabric with an alkaline boil wash. In this treatment, the individual fabrics were boiled for 3 hours in an alkaline wash liquid and subsequently dried. The wash liquid comprised 1 liter of water, 1 g of trisodium phosphate and 2 g of a fatty acid polyglycol ester obtained by ethoxylating 1,4-butanediol with 15 mol of ethylene oxide and subsequently esterifying the ethoxylate with 1 mol of oleic acid.

In Examples VII to XIV, the compounds according to the invention B7 to B14 were tested by means of a conventional spin finish for polyamide fibers, which contained in each case about 150 g of the compound according to the invention per 1,000 g of spin finish (the spin finish thus comprised water as main component, the customary ethoxylated fatty alcohols and long-chain amine oxides as finishes and about 15% by weight of compound according to the invention). Each of the eight spin finishes was used to treat identical nylon-6 filaments in each case in order to apply to the filaments as much of the compound according to the invention and the finish that 0.05% by weight of fluorine and 1% by weight of finish were present on the filaments, percentages by weight being in each case based on the weight of the filaments. To this end, the filaments were pulled in conventional manner through the spin finish, dried and maintained at a temperature of 200° C. for 30 seconds (heat treatment, condensation). The filaments thus treated were each turned into a fabric. Eight fabrics with the compounds according to the invention B7 to B14 were present, each fabric having a fluorine add-on of 0.05% by weight and a finish add-on of 1% by weight, percentages by weight being in each case based on the weight of the fabric.

The eight fabrics were tested for oil repellency and water repellency as described above.

Results of Examples I to XIV are summarized below.

| Example and tested compounds | Oil repellency after the condensation | Oil repellency after the boil wash | Water repellency after the condensation | Water repellency after the boil wash |
| --- | --- | --- | --- | --- |
| I/B1 | 6 | 5 | 5 | 5 |
| II/B2 | 5 | 5 | 5 | 5 |
| III/B3 | 5 | 5 | 5 | 5 |
| IV/B4 | 6 | 5 | 5 | 4 |
| V/B5 | 5 | 4 | 5 | 5 |
| VI/B6 | 6 | 5 | 5 | 4 |
| VII/B7 | 6 | 4 | 5 | 5 |
| VIII/B8 | 5 | 4 | 4 | 4 |
| IX/B9 | 5 | 4 | 4 | 4 |
| X/B10 | 5 | 4 | 5 | 4 |
| XI/B11 | 6 | 5 | 4 | 4 |
| XII/B12 | 5 | 4 | 4 | 4 |
| XIII/B13 | 5 | 4 | 4 | 4 |
| XIV/B14 | 6 | 4 | 4 | 4 |

In what follows, the AATCC test 118—1966 (American Association of Textile Chemists and Colorists) and DIN 53,888—1965 (German Industrial Standard) are described:

To determine the oil repellency value in accordance with AATCC test 118—1966, three drops of a certain test liquid (see below) are carefully placed on the textile material under test.

Exposure time: 30 seconds. The value quoted is that at which no apparent wetting of the fabric underneath the drops (after expired exposure time) has been caused:

| Test liquid | Oil repellency value |
| --- | --- |
| Paraffin oil | 1 |
| Paraffin oil:n-hexadecane = 65:35 | 2 |
| n-Hexadecane | 3 |
| n-Tetradecane | 4 |
| n-Dodecane | 5 |
| n-Decane | 6 |
| n-Octane | 7 |
| n-Heptane | 8 |

An oil repellency value of 1 signifies the worst and an oil repellency value of 8 the best repellency effect.

To determine the water repellency value in accordance with DIN 53,888—1965, the textiles under test are exposed under standardized conditions to artificial rain, while at the same time the underside of the textile sample is mechanically rubbed. The water bead-off effect is assessed visually on a scale from 1 to 5, 1 signifying the worst and 5 the best bead-off effect.

The test results show that the urethanes according to the invention produce a very high oil and water repellency and that the urethanes according to the invention can also be added to textile treatment finishes.

We claim:

1. A urethane which contains perfluoroalkyl groups, epichlorohydrin groups and dialcohol radicals and has the following formula 1

$$\left[ R_f-(CH_2)_x-O-(CH_2-CH-O)_y-\overset{O}{\overset{\|}{C}}-\overset{H}{\overset{|}{N}}- \atop CH_2Cl \right]_m$$

$$-A-\left[\overset{H}{\overset{|}{N}}-\overset{O}{\overset{\|}{C}}-(OR)_z-O-B\right]_n;$$

in which $R_f$ denotes a perfluoroalkyl group, having 4 to 20 carbon atoms or an $R'_f SO_2NR_1$ group in which $R'_f$ is a perfluoroalkyl group having 4 to 20 carbon atoms and $R_1$ is H or an alkyl group having 1 to 4 carbon atoms, x is a whole number from 1 to 4, y is a number from 1 to 10, z is a number from 1 to 25 m is a number from 1 to 2 and n is a number from 1 to 2, the sum of m+n being at most 3, A denotes one of the groups conforming to the following formulae 2 to 10:

-continued

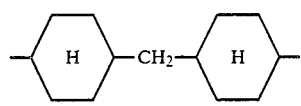

(5)

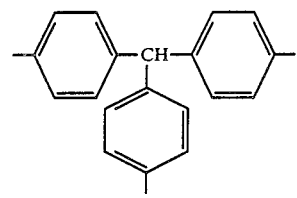

(6)

$+CH_2 +_6$ (7)

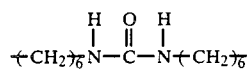
(8)

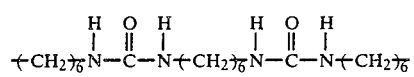
(9)

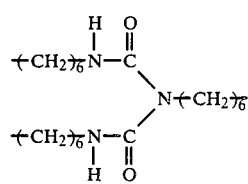
(10)

R denotes an alkylene group having 2 to 6 carbon atoms, the chloromethylethylene group or a group of the formula —CH(CH$_2$OCH$_2$CH$_2$—C$_4$F$_9$ to C$_{20}$F$_{41}$)—CH$_2$—, where R can also have more than one of these meanings if z is greater than 1, and B denotes the hydrogen atom, an alkyl group having 1 to 4 carbon atoms or a group conforming to the following formula 11

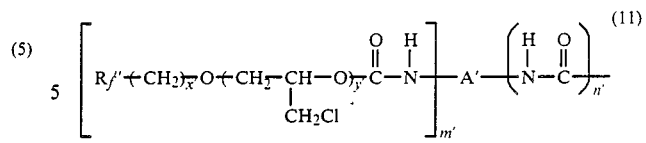
(11)

in which R$_f'$, x', y', m', n' and A' have one of the meanings of R$_f$, x, y, m, n and A, respectively.

2. The urethane as claimed in claim 1, wherein
R$_f$ denotes a perfluoroalkyl group having 6 to 16 carbon atoms,
x denotes 2,
y denotes 1 to 5,
z denotes 1 to 20,
m denotes 1 to 2,
n denotes 1 to 2, the sum m+n being at most 3,
A denotes a toluylene group or one of the three groups conforming to the formulae 8 to 10,
R denotes an ethylene, propylene, butylene or a chloromethylethylene group, where R can also have more than one of these meanings if z is greater than 1, and
B denotes H, an alkyl group having 1 to 4 carbon atoms or a group conforming to the formula 11, where A' is a toluylene group or one of the three groups conforming to the formulae 8 to 10.

3. The urethane as claimed in claim 1, wherein
R$_f$ denotes a perfluoroalkyl group having 6 to 16 carbon atoms,
x denotes 2,
y denotes 1 to 5,
z denotes 1 to 20,
m denotes 1 to 2,
n denotes 1 to 2, the sum of m +n being at most 3,
A denotes a toluylene group or one of the three groups conforming to the formula 8 to 10,
R denotes an ethylene, propylene, butylene or a chloromethylethylene group and in the case of z being greater than 1 also an ethylene and propylene group, and
B denotes H, an alkyl group having 1 to 4 carbon atoms or a group conforming to the formula 11, where A' is a toluylene group or one of the three groups conforming to the formulae 8 to 10, R$_f''$ is a perfluoroalkyl group having 6 to 16 carbon atoms, x' is 2, y' is 1 to 5, m' is 1 to 2 and n' is 1 to 2, the sum m'+n' being at most 3.

* * * * *